United States Patent
Van Ess

[19]

[11] Patent Number: 6,007,554
[45] Date of Patent: Dec. 28, 1999

[54] SURGICAL CUTTER

[76] Inventor: Lester Jay Van Ess, 51 Lawrence La., Bay Shore, N.Y. 11706

[21] Appl. No.: 09/146,147

[22] Filed: Sep. 3, 1998

[51] Int. Cl.$^6$ .................................................. A61B 17/32
[52] U.S. Cl. .......................... 606/167; 606/170; 606/174; 604/22
[58] Field of Search .................................. 606/159, 169, 606/107, 167, 168, 170, 172, 174, 175, 180, 181, 182, 185; 604/22

[56] References Cited

U.S. PATENT DOCUMENTS 5,667,519  9/1997  Ramsey .

*Primary Examiner*—Michael Buiz
*Assistant Examiner*—Lien Ngo
*Attorney, Agent, or Firm*—Collard & Roe, PC

[57] ABSTRACT

A cutter for enlarging an incision made during laparoscopic surgery comprising an outer tube having an open end, a closed end, and two longitudinally extending opposing slots therein and an inner tube slidably disposed within the outer tube and having two handles extending through the slots in the outer tube. An elongated hollow blade sheath is connected to the inner tube and extends out of the opening of the outer tube. One longitudinal edge of the sheath is open and there is a cutout along the open side edge near the end of the sheath. There is an elongated blade connected to the outer tube and disposed within the blade sheath. The blade is shorter than the blade sheath and has a cutting edge along its short end. There is a compression spring connecting the inner tube to the blade, so that pulling the handles toward the closed end of the outer tube causes the blade sheath to retract and expose the blade in the cutout of the blade sheath. Releasing the handles causes the blade sheath to extend and cover the blade. The cutter allows for controlled and defined enlargement of a laparoscopic incision for removal of a gall bladder without rupturing the gall bladder.

7 Claims, 5 Drawing Sheets

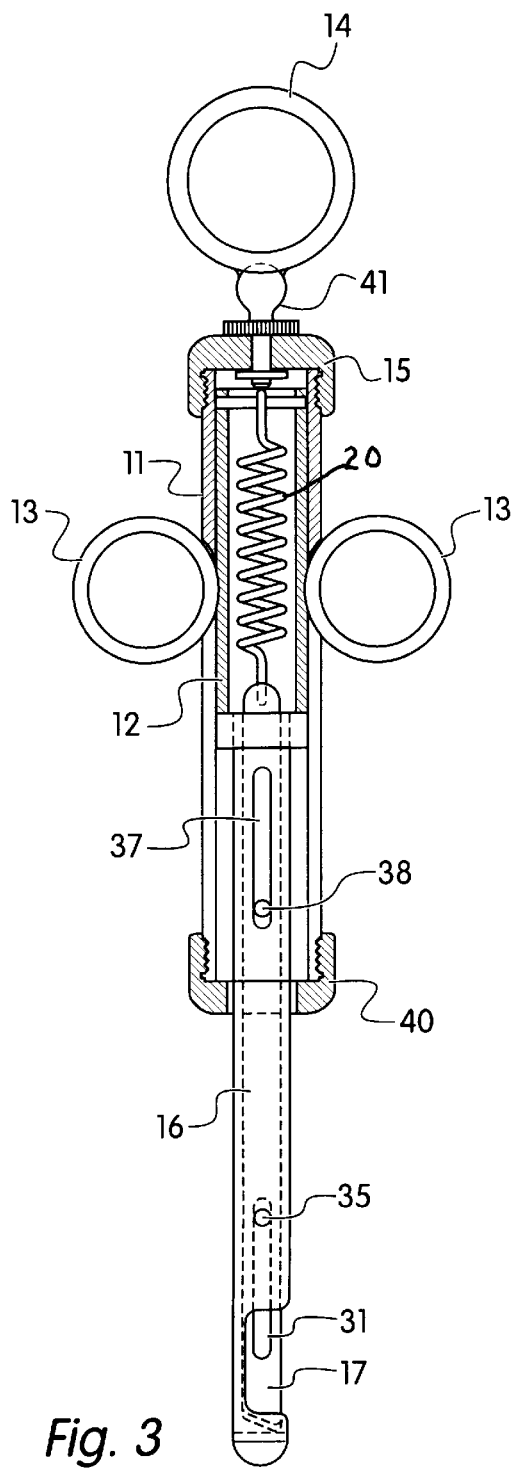
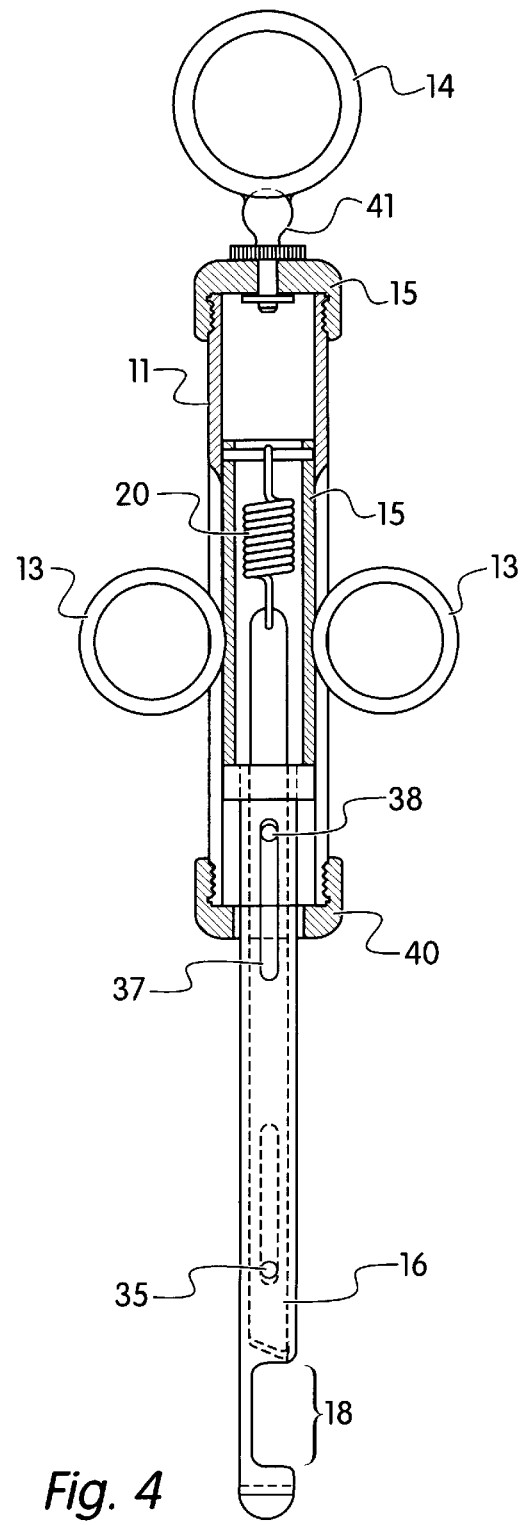
Fig. 3
Fig. 4

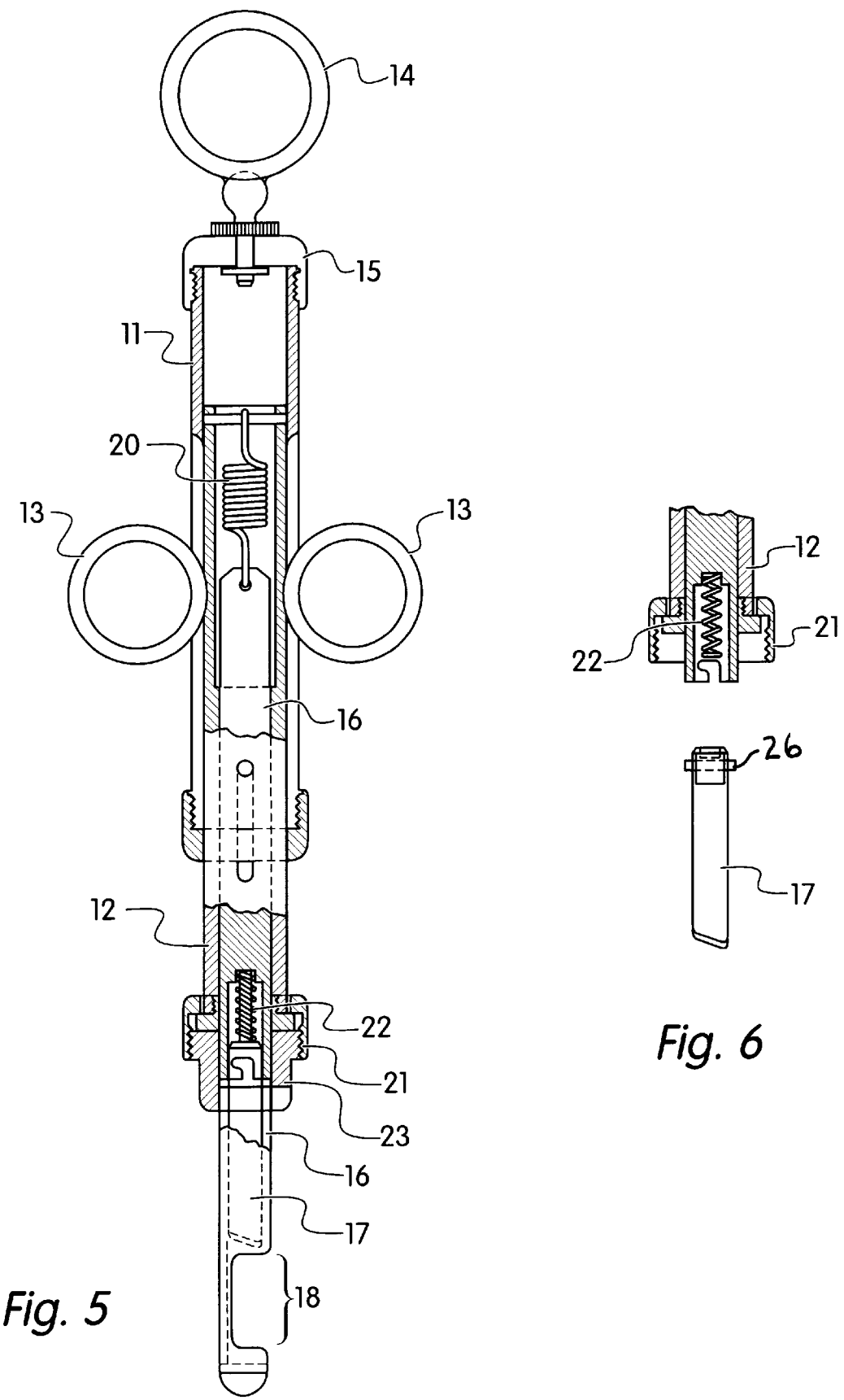

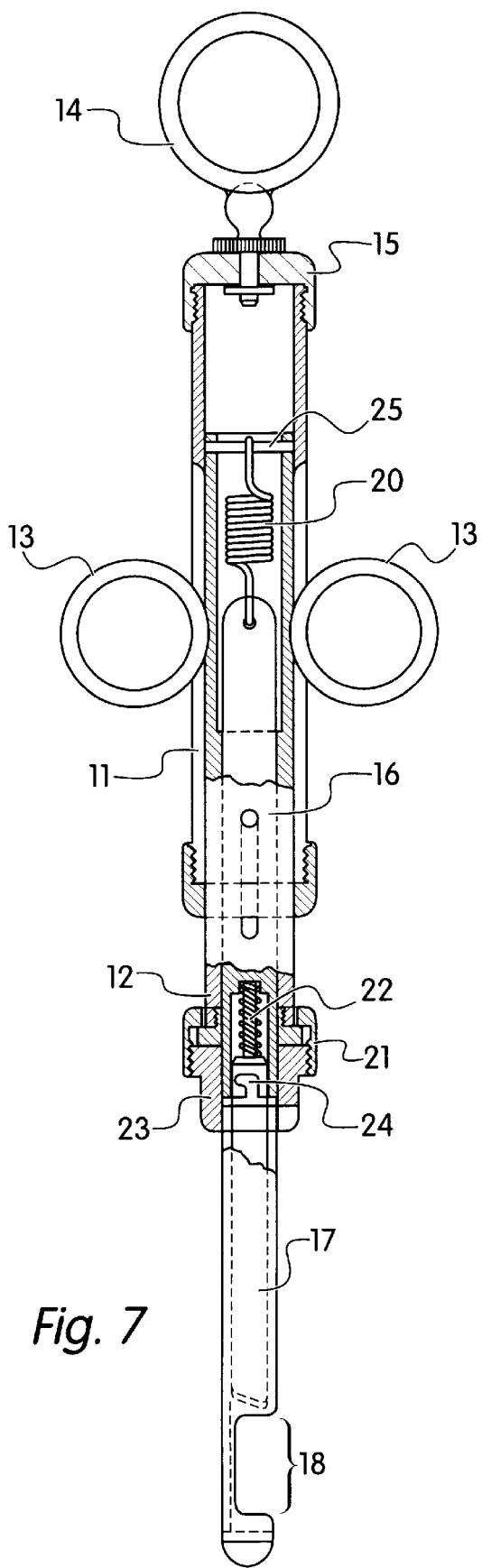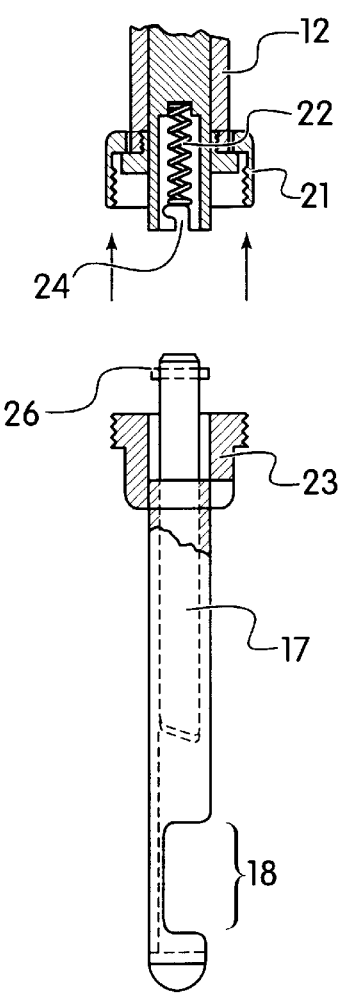
Fig. 7
Fig. 8

SURGICAL CUTTER

BACKGROUND OF THE INVENTION

1. Field of the Invention

This invention relates to a surgical cutter for use in laparoscopic surgery. In particular, the invention relates to a device for enlarging the incision made during laparoscopic surgery to allow for the removal of items larger than the incision, such as a gall bladder.

2. The Prior Art

Laparoscopic cholecystectomy, or gall bladder removal, is initiated by making a 10–12 mm incision just beneath the umbilicus. A video camera is then placed through this incision during the surgery. Upon completion of the operation, the gall bladder is removed through this 10–12 mm incision. When the gall bladder is very large or is swollen from inflammation, it cannot be removed from this incision and becomes lodged. This requires the placement of retractors for exposure, a clamp beneath the fascia and an incision over the clamp with a scalpel to enlarge the fascia. However, use of an ordinary surgeon's knife or scalpel to enlarge an endoscopic incision is not acceptable because of the hazard of making an incision of uncontrolled length and of the hazard of damaging the gall bladder.

A second technique used for an entrapped gall bladder is to open the gall bladder at the top portion protruding from the incision and empty the gall bladder until its contents are reduced to the point where the gall bladder is small enough to be withdrawn from the incision. However, this technique is undesirable because the gall bladder contents, including stones and bile, are at times spilled on the abdominal wall of the patient.

One type of device used to enlarge the incision to allow for passage of the entire gall bladder is shown in U.S. Pat. No. 5,667,519 to Ramsey. This device comprises a handle having a blade resting on a guide with a semicircular cross section. The guide fits along the cannula and guides the blade downward in a controlled manner.

SUMMARY OF THE INVENTION

It is therefore an object of the present invention to provide a device for enlarging the incision during a laparoscopic cholecystectomy that allows for cutting in a controlled and defined manner.

It is another object of the present invention to provide a device for enlarging a laparoscopic incision during a cholecystectomy that does not damage the gall bladder being extracted.

It is yet another object of the present invention to provide a device for enlarging a laparoscopic incision that is simple to manufacture and use.

These and other objects are accomplished by a cutter for enlarging an incision made during laparoscopic surgery, comprising an outer tube having an open end, a closed end, and two longitudinally extending opposing slots therein and an inner tube slidably disposed within the outer tube and having two handles extending through the slots in the outer tube. An elongated hollow blade sheath is connected to the inner tube and extends out of the opening of the outer tube. One longitudinal edge of the sheath is open and there is a cutout along the open edge near the end of the sheath.

There is an elongated blade connected to the outer tube and disposed within the blade sheath. The blade is shorter than the blade sheath and has a cutting edge along its short end. There is an extension spring disposed in the inner tube and connected to the blade, so that pulling the handles toward the closed end of the outer tube causes the spring to extend and blade sheath to retract and expose the blade in the cutout of the blade sheath. Releasing the handles causes the blade sheath to extend and cover the blade, with the spring returning to its compressed position. The cutter allows for controlled and defined enlargement of a laparoscopic incision for removal of a gall bladder without rupturing the gall bladder.

The handles are preferably ring shaped, for the greatest ease of use and comfort. However, other shapes could also be used. There is preferably a ring-shaped handle pivotally mounted on the closed end of the outer tube. This handle provides a place for the surgeon's thumb and provides leverage for pulling the other two ring shaped handles back to retract the blade sheath.

The blade is preferably removably connected to the cutter, so that it can be easily replaced and cleaned or sharpened. In a preferred embodiment, the blade is connected via two laterally extending buttons on an end of the blade opposite the cutting edge, and two L-shaped grooves in the open end of the outer tube. The blade is attached to the outer tube by sliding the buttons into the L-shaped grooves and partially rotating the outer tube.

The cutout in the blade sheath is preferably about 0.75 in. long and about 0.19 in. wide. In a preferred embodiment, the blade sheath is removably connected to the inner tube. This removable connection comprises a threaded top portion on the blade sheath, and a threaded nut surrounding the inner tube. The top portion of the sheath is screwed into the threaded nut on the inner tube to connect the sheath to the cutter.

Alternatively, both the blade and the blade sheath can be permanently fixed in the cutter.

The cutter is kept in an extended position whereby the blade is hidden within the blade sheath in a resting state. Pulling on the handles causes the spring to expand and the blade sheath to retract, exposing the blade for cutting. Releasing the handles cause the spring to return to its normal compressed state and the sheath to extend back around the blade.

Preferably, the blade sheath has a longitudinal slot running through it. A pin is disposed through the slot and the blade and is attached to the outer tube. This pin guides the sheath in a straight line fashion as it is being retracted and extended and ensures smooth operation of the cutter. This pin also attaches the blade to the outer tube and renders it stationary. In addition, the blade preferably has a slot therethrough at a lower portion, through which a guide pin attached to the blade housing is extended. This is also to ensure smooth traveling of the blade.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 3 shows a side cross-sectional view of the surgical cutter according to FIG. 1 in the extended position;

FIG. 4 shows a cross-sectional view of the surgical cutter according to FIG. 3 in the retracted position;

FIG. 5 shows a cross-sectional view of an alternative embodiment of the cutter according to the invention;

FIG. 6 shows a cross-sectional view of the blade housing connection to the device in the embodiment of FIG. 5;

FIG. 7 shows a cross sectional view of the embodiment of FIG. 5;

FIG. 8 shows a cross sectional view of the blade sheath connection to the cutter in the embodiment of FIG. 5.

DETAILED DESCRIPTION OF THE PREFERRED EMBODIMENT

Figure 1:
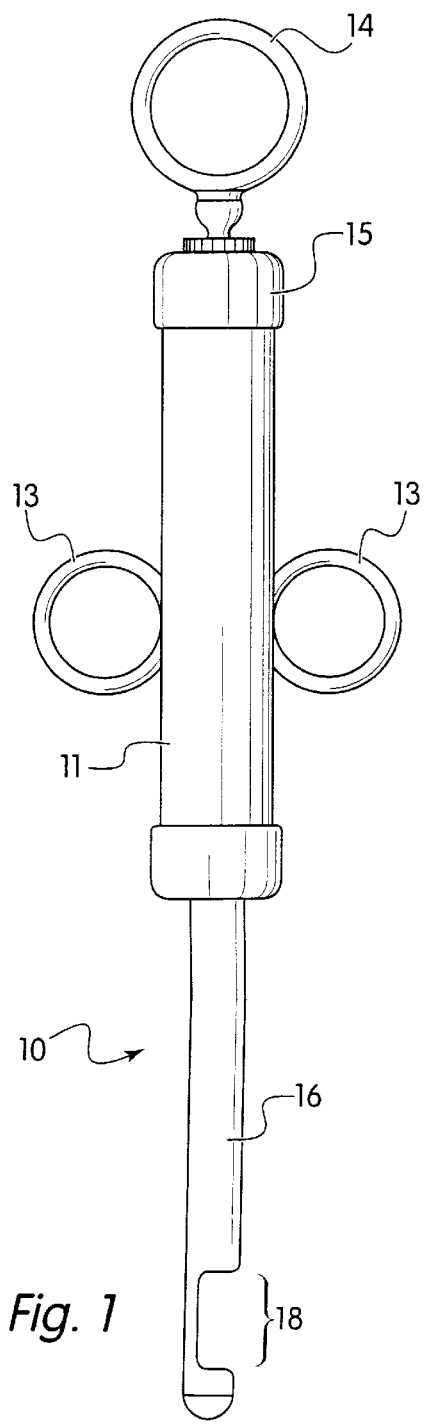
FIG. 1 shows a side view of the surgical cutter according to the invention in an extended position.
Figure 2:
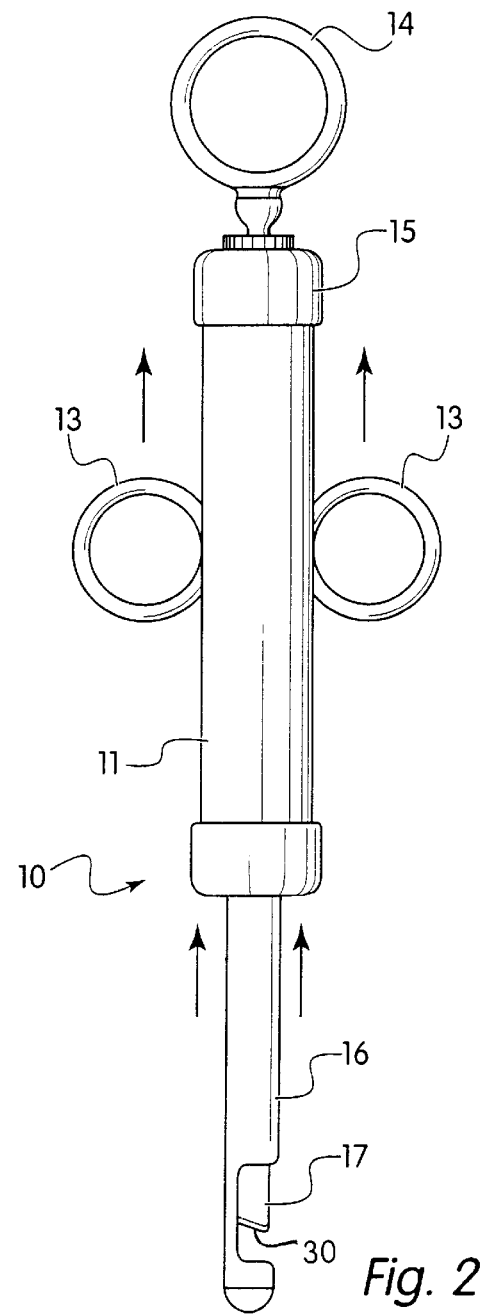
FIG. 2 shows a side view of the surgical cutter according to FIG. 1 in the retracted position.
Figure 9:
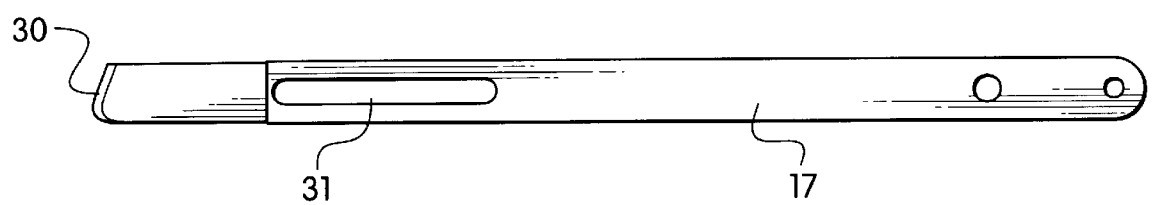
FIG. 9 shows a side view of the blade in the embodiment according to FIG. 3.

Referring now in detail to the drawings and, in particular, FIGS. 1 and 2, there is shown the surgical cutter 10 according to the invention in an extended, resting position in FIG. 1, and in a retracted, cutting position in FIG. 2. Cutter 10 has an outer tube 11 having two slots therein for ring-shaped handles 13 to extend therethrough. A larger ring-shaped handle 14 is pivotally mounted via a supporting member 41 to an end cap 15 on one end of outer tube 11. The other end of outer tube 11 is covered by an end cap 40. A blade sheath 16 extends out from the other end of outer tube 11. As shown in FIG. 2, pulling handles 13 back causes blade sheath 16 to retract and expose a blade 17 within a cutout 18 of blade sheath 16. Cutout 18 is preferably about 0.75 in. long and about 0.19 in. wide.

The mechanics of cutter 10 are shown in FIGS. 3 and 4, which show cross-sectional views of cutter 10. Within outer tube 11 there is an inner tube 12 that is slidable within outer tube 11. Blade sheath 16 is attached to inner tube 12 and slides within outer tube 11 as ring-shaped handles 13 are pulled back. Blade 17 is disposed within blade sheath 16 and is fixedly attached to outer tube 11 by a screw 38. Blade sheath 16 has a slot 37 that allows it to slide despite the presence of screw 38. An extension spring 20 is connected to blade 17 at one end and to inner tube 12 at another end. Pulling handles 13 back causes inner tube 11 to slide backward and stretch spring 20, as shown in FIG. 3. Releasing handles 13 causes spring 20 to return to a compressed position as shown in FIG. 4.

Blade 17 has a slot 31 cut therethrough for accommodating a screw 35 that extends through slot 31 and is secured on either side of blade sheath 16. Slot 31 ensures that blade sheath 16 will slide in a straight path along blade 17 when handles 13 are pulled. Details of the configuration of blade 17 are shown in FIG. 7. Blade tip 30 is preferably angled to give a guillotine like cut.

The entire device is preferably made of stainless steel, but other materials could also be used.

An alternative embodiment of cutter 10 is shown in FIGS. 3–6. In this embodiment, blade sheath 16 and blade 17 are easily detachable from cutter 10, so that a new blade can be used each time, or for cleaning and sharpening purposes. In this embodiment, blade 17 is connected to outer tube 11 via two pins on the end of blade 17 that fit into a slot 24 on cutter 10. Blade 17 is inserted into slot 24 and turned so that it fits securely in slot 24. A compression spring 22 is placed directly above slot 24 and keeps blade 17 securely in slot 24, so that it cannot become inadvertently disengaged.

Blade sheath 16 is also removable, as shown in FIG. 6. Blade sheath 16 has a threaded coupling 23 that can be screwed into a threaded nut 21 disposed on inner tube 12.

Accordingly, while only a few embodiments of the present invention have been shown and described, it is obvious that many changes and modifications may be made there unto without departing from the spirit and scope of the invention.

What is claimed is:

1. A cutter for enlarging an incision made during laparoscopic surgery, comprising:

an outer tube having an open end, a closed end, and two longitudinally extending opposing slots therein;

an inner tube slidably disposed within the outer tube and having two handles extending through the slots in the outer tube;

an elongated hollow blade sheath connected to the inner tube and extending out of the opening of the outer tube, said sheath having two side edges, one side edge being open, and a free end, and a cutout along the open side edge near said free end;

an elongated blade connected to the outer tube and disposed within the blade sheath, said blade being shorter than said blade sheath and having two longitudinal edges and a cutting edge;

an extension spring disposed within the inner tube, said extension spring connecting the inner tube to the blade;

wherein pulling the handles toward the closed end of the outer tube causes the spring to expand and the blade sheath to retract and expose the blade in the cutout of the blade sheath, and releasing the handles causes the blade sheath to extend and cover the blade.

2. The cutter according to claim 1, wherein the handles are ring shaped.

3. The cutter according to claim 2, wherein the closed end of the outer tube has a ring-shaped handle pivotally mounted thereon.

4. The cutter according to claim 1, wherein the blade is removable.

5. The cutter according to claim 4, wherein the removable connection comprises two laterally extending buttons on an end of the blade opposite the cutting edge, and two L-shaped grooves in the cutter, wherein the blade is attached by sliding the buttons into the L-shaped grooves and partially rotating the grooves.

6. The cutter according to claim 1, wherein the cutout in the blade sheath is about 0.75 in. long and about 0.19 in. wide.

7. The cutter according to claim 1, wherein the blade sheath has a threaded top portion and is removably connected to a threaded nut surrounding the inner tube.

* * * * *